United States Patent [19]

Clitherow et al.

[11] Patent Number: 5,399,556
[45] Date of Patent: Mar. 21, 1995

[54] CARBOXYLIC ACID DERIVATIVES

[75] Inventors: John W. Clitherow, Sawbridgeworth; Eric W. Collington, Knebworth, both of England

[73] Assignee: Glaxo Group Ltd., London, England

[21] Appl. No.: 938,301

[22] Filed: Mar. 2, 1992

Related U.S. Application Data

[63] Continuation of Ser. No. 660,746, Feb. 26, 1991, abandoned.

[30] Foreign Application Priority Data

Feb. 27, 1990 [GB] United Kingdom ............... 9004328

[51] Int. Cl.$^6$ .................. A61K 31/555; C07D 307/52
[52] U.S. Cl. ................................ 514/184; 549/206; 549/495
[58] Field of Search .................. 549/206, 495; 514/184

[56] References Cited

U.S. PATENT DOCUMENTS

| | | | |
|---|---|---|---|
| 5,008,256 | 4/1991 | Clitherow | 549/206 |
| 5,041,557 | 8/1991 | Vinas | 549/206 |

FOREIGN PATENT DOCUMENTS

| | | |
|---|---|---|
| 0350422A1 | 5/1989 | European Pat. Off. . |
| 0351348A2 | 5/1989 | European Pat. Off. . |
| 0387177A2 | 9/1989 | European Pat. Off. . |
| 8804023 | 12/1988 | Spain . |
| 1565966 | 4/1980 | United Kingdom . |
| 2218987 | 11/1989 | United Kingdom . |

OTHER PUBLICATIONS

Answer 1, Copyright 1991 American Chemical Society, d acc 100:96486v ab.

Current Trends Review, Drug Development Research 17:185–197 (1989): "Current Views of Zinc as a Gastro-hepatic Protective Agent" by C. H. Cho, Dept. of Pharmacology, University of Hong Kong.

Drugs Exptl. Clin. Res. XV(2) 83–89 (1989), "Zinc Compounds, A New Treatment in Peptic Ulcer" by Escolar G. Bulbena O., Dept. of Pharmacology, Laboratorios Vinas S.A., Torrente Vidalet 29, 08012 Barcelona, Spain.

*Primary Examiner*—C. Warren Ivy
*Assistant Examiner*—A. A. Owens
*Attorney, Agent, or Firm*—Bacon & Thomas

[57] ABSTRACT

The invention relates to salts formed between ranitidine and a complex of zinc with a carboxylic acid selected from tartaric acid, citric acid and alkyl citric acids, and to solvates of such salts. The salts and solvates thereof are useful in the treatment of gastro-intestinal disorders, such as peptic ulcer disease and non-ulcer dyspepsia.

8 Claims, No Drawings

CARBOXYLIC ACID DERIVATIVES

This application is a continuation of application Ser. No. 07/660,746, filed Feb. 26, 1991, now abandoned.

This invention relates to salts of a furan derivative having action on histamine receptors, to a process for the preparation thereof, to pharmaceutical compositions containing them and to their use in therapeutics. More particularly the invention is concerned with salts of ranitidine formed with zinc complexes of carboxylic acids.

Ranitidine is the approved name for N-[2-[[[5-[(dimethylamino)- methyl]-2-furanyl]methyl]thio]ethyl]-N'-methyl-2-nitro-1,1-ethenediamine which, together with its physiologically acceptable salts, is described and claimed in British Patent Specification No. 1565966. Reference is made in British Patent Specification No. 1565966 to physiologically acceptable salts formed with inorganic and organic acids. Such salts include hydrochlorides, hydrobromides and sulphates, and salts formed with aliphatic mono- and di-carboxylic acids such as acetates, maleates and fumarates.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Zinc compounds such as zinc chloride, zinc sulphates and zinc acexamate have been described in for example Drug Development Research 17, 185–197 (1989) and Drugs Exptl. Clin. Res. XV(2), 83–89 (1989) as being gastrohepatic protective agents, having a stabilising action on mast cells, preserving gastric mucus and protecting the gastric mucosa against the actions of known gastric irritants. Such zinc compounds thus have a role in the treatment of gastric ulceration.

The only known stable form of zinc citrate is the 3:2 complex formed between zinc and citric acid $Zn_3(C_6H_5O_7)_2 \cdot 2H_2O$, and this has been incorporated into toothpaste preparations as an antibacterial and antiplaque agent.

It has now suprisingly been found that the basic $H_2$-receptor antagonist ranitidine will form a stable salt with a simple 1:1 stoichiometric complex of zinc and a carboxylic acid such as citric acid, and that the salt thus formed possesses a useful and advantageous profile of activity.

The present invention thus provides novel salts of ranitidine and a complex of zinc with a carboxylic acid selected from tartaric acid, citric acid or an alkyl citric acid, and solvates of such salts.

The alkyl citric acid may be for example a $C_{1-6}$ alkyl citric acid, more particularly a $C_{1-3}$ alkyl citric acid (e.g. propylcitric acid).

In instances where the carboxylic acid can exhibit optical and/or geometrical isomerism, the invention is intended to include all optical isomers including racemates, and/or geometric isomers. Solvates, including hydrates, are also included within the scope of the invention.

The preferred carboxylic acid for use in the invention is citric acid.

A particularly preferred compound according to the invention is N-[2-[[[5-[(dimethylamino)methyl]-2-furanyl]methyl]thio]ethyl]-N'- methyl- 2-nitro- 1,1-ethenediamine 2-hydroxy-1,2,3-propanetricarboxylate zinc (2+) complex, more specifically a 1:1 complex, also known as ranitidine zinc citrate.

Salts according to the invention possess a particularly advantageous combination of properties for the treatment of gastrointestinal disorders, especially peptic ulcer disease and other gastroduodenal conditions, for example non-ulcer dyspepsia.

Salts according to the invention possess antisecretory and cytoprotective properties. Antisecretory activity has been demonstrated in vivo against histamine-induced gastric acid secretion in the Heidenhain pouch dog. Cytoprotective activity has been demonstrated in vivo by the ability of the salts to inhibit ethanol-induced gastric lesions in rats.

A further feature of salts according to the invention is that they are water soluble and give stable aqueous solutions.

The salts of the invention are distinct chemical entities, and this may be demonstrated on the basis of, for example, infra-red spectroscopy. Thus for instance, the infra-red spectrum of ranitidine zinc citrate was quite distinct from the infra-red spectrum of a simple physical mixture of ranitidine and zinc citrate.

Salts according to the invention may also be prepared by reacting ranitidine with an appropriate zinc-carboxylic acid complex (e.g. zinc citrate) in a suitable solvent such as water, and separating the salt thus formed from the solution.

According to a further aspect the invention provides a salt of ranitidine and a complex of zinc with tartaric acid, citric acid, or an alkyl citric acid, including solvates of such salts, said salt being prepared by reacting ranitidine with an appropriate zinc-carboxylic acid complex.

According to one particular further aspect, the invention provides ranitidine zinc citrate, including solvates thereof when prepared by reacting ranitidine with a complex of zinc with citric acid.

The reaction between ranitidine and an appropriate zinc-carboxylic acid complex to give a salt according to the invention is preferably carried out at a temperature within the range of 20° to 600° C., more preferably at room temperature. The resulting solution is cooled (if appropriate) and filtered, and the required ranitidine salt may be obtained from the filtrate, by evaporation followed by extraction and trituration of the resulting residue using for example an alcohol e.g. methanol or ethanol, a ketone e.g. acetone or an ether e.g. diethyl ether.

The intermediate zinc-carboxylic acid complex may be prepared by reacting a zinc base (e.g. zinc oxide or zinc carbonate) with an appropriate carboxylic acid (e.g. citric acid) in a solvent such as water, conveniently at a temperature within the range of 20° to 60°.

The intermediate zinc-carboxylic acid complex is preferably formed in situ and immediately reacted with ranitidine to give a salt according to the invention.

The salts according to the invention may be formulated for administration in any convenient way and the invention includes within its scope pharmaceutical compositions containing a salt according to the invention adapted for use in human or veterinary medicine. Such compositions, which are primarily intended for oral administration, may be formulated in a conventional manner using one or more pharmaceutically acceptable carriers or excipients.

For oral administration, the pharmaceutical compositions may take the form of, for example, tablets (including chewable or suckable tablets) or capsules (which may be of the hard or soft type). Such compositions may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disinterants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Tablets represent a preferred type of composition for oral use.

A proposed dose of the salts of the invention for internal administration to man is 80 mg to 1.4 g, preferably 250 mg to 1 g, of the active ingredient per unit dose. The unit dose may be administered, for example, one to four times daily, preferably once or twice. The exact dose will depend on the nature and severity of the condition being treated, and it will also be appreciated that it may be necessary to make routine variations to the dosage depending on the age and weight of the patient.

The invention is illustrated by the following Example in which temperatures are in 0° C. Thin layer chromatography (t.l.c.) was carried out on silica, eluting with the solvent system indicated, and using u.v., iodoplatinate, potassium permanganate and bromocresol green stain for detection.

EXAMPLE

N-[2-[[[5-[(Dimethylamino)methyl]-2-furanyl]methyl]-thio]ethyl]-N'-methyl-2-nitro-1,1-ethenediamine [2-hydroxy,1,2,3-propanetricarboxylate zinc (2+) complex (1:1)](1:1) ["Ranitidine zinc citrate"(1:1:1)]

To a solution of 2-hydroxy-1,2,3-propanetricarboxylic acid (citric acid, 2.10 g) in water (10 ml) was added zinc oxide (0.81 g) and the solid dispersed and dissolved by warming to about 60°. To the clear solution was added N-[2-[[[5dimethylamino)methyl]-2-furanyl]methyl]thio]ethyl]-N'-methyl-2-nitro- 1,1-ethenediamine (ranitidine, 6.25 g) and the solid dissolved. The solution was filtered and the flitrate evaporated to dryness in vacuo to give a gummy residue. This was redissolved in water (50 ml), the fine suspension filtered through Hyflo and the filtrate evaporated to dryness in vacuo to give a gummy residue. This was mixed with hot methanol (50 ml) and the mixture evaporated to dryness in vacuo. The residue was suspended in hot methanol (70 ml), filtered and the residue washed well with hot methanol (~ 100 ml) then acetone and ether and dried to give the title compound (3.93 g).

T.l.c. (methylene chloride: ethanol: 0.88 ammonia; 50:8:1 ) Rf 0.45 (ranitidine) and Rf zero (zinc citrate).

T.l.c. (Chloroform: methanol: acetic acid: water; 15:5:1:1) Rf 0.25 (ranitidine) and Rf zero (zinc citrate).

Analysis Found: C,39.47; H,5.19; N,10.05; 0.28.68; S,5.71. $C_{13}H_{23}N_4O_3S:C_6H_5O_7Zn:H_2O$; 1:1:0.26 requires C,39.72; H,5.00: N,9.75; O,28.57; S,5.58% Water assay indicated 0.83% $H_2O=0.046mol$ %==0.26 mol. N.m.r. indicated zinc citrate: ranitidine, 1:1.

The following Examples A to C illustrate pharmaceutical compositions according to the invention in which the active ingredient is in particular ranitidine zinc citrate. Other compounds according to the invention may be formulated in a similar manner.

EXAMPLE A TABLETS

Tablets may be prepared by the normal methods such as direct compression or wet granulation.

The tablets may be film coated with suitable film forming materials, such as hydroxypropyl methylcellulose, using standard techniques.

| (i) Direct Compression | mg/tablet |
|---|---|
| Active ingredient | 270 |
| Lactose | 105 |
| Microcrystalline Cellulose | 100 |
| Cross-linked Polyvinylpyrrolidone | 20 |
| Magnesium Stearate | 5 |
| Compression weight | 500 mg |

The active ingredient, microcrystalline cellulose, lactose and cross-linked polyvinylpyrrolidone are sieved through a 500 μm sieve and blended in a suitable mixer. The magnesium stearate is sieved through a 250 μm sieve and blended with the active blend. The blend is compressed into tablets using suitable punches.

| (ii) Wet Granulation | mg/tablet |
|---|---|
| Active ingredient | 270 |
| Lactose | 155 |
| Pregelatinised Starch | 50 |
| Cross-linked Polyvinylpyrrolidone | 20 |
| Magnesium Stearate | 5 |
| Compression weight | 500 mg |

The active ingredient, lactose and pregelatinised starch are blended together and granulated with water. The wet mass is dried and milled. The magnesium stearate and cross-linked polyvinylpyrrolidone are screened through a 250 μm sieve and blended with the granule. The resultant blend is compressed using suitable tablet punches.

EXAMPLE B CAPSULES

| | mg/capsule |
|---|---|
| Active ingedient | 270 |
| Lactose | 47 |
| Polyvinylpyrrolidone | 15 |
| Cross-linked Polyvinylpyrrolidone | 15 |
| Magnesium Stearate | 3 |
| Fill weight | 350 mg |

The active ingredient and lactose are blended together and wet massed with a solution of polyvinylpyrrolidone. The mass is dried and milled and blended with cross-linked polyvinylpyrrolidone and magnesium stearate (screened through a 250 μm mesh). The resultant blend is filled into hard gelatin capsules of a suitable size.

EXAMPLE C ORAL SYRUP

| Active ingedient | 270 mg |
|---|---|
| Hydroxypropyl Methylcellulose | 45 mg |
| Propyl Hydroxybenzoate | 1.5 mg |
| Butyl Hydroxybenzoate | 0.75 mg |
| Saccharin Sodium | 5.0 mg |
| Sorbitol Solution | 1.0 ml |
| Suitable Buffers | qs |
| Suitable Flavours | qs |
| Purified Water to | 10.0 ml |

The hydroxpropyl methylcellulose is dispersed in a portion of hot purified water together with the hydroxybenzoates and the solution is allowed to cool to room temperature. The saccharin sodium, flavours and sorbitol solution are added to the bulk solution. The active ingredient is dissolved in a portion of the remaining water and added to the bulk solution. Suitable buffers may be added to control the pH in the region of maximum stability. The solution is made up to volume, filtered and filled into suitable containers.

We claim:

1. A salt formed between one mole of ranitidine and a 1:1 molar complex of zinc with a carboxylic acid selected from the group consisting of citric acid and alkyl citric acids: or a solvate of such a salt.

2. The salt of claim 1 wherein the alkyl group of the alkyl citric acid is a $C_1-C_6$ alkyl group.

3. The compound of claim 1 wherein the carboxylic acid is citric acid.

4. The compound of claim 1 wherein the carboxylic acid is a $C_1-C_6$ alkyl citric acid.

5. A pharmaceutical composition for the treatment of a gastrointestinal disorder comprising an effective amount of a salt defined by claim 1 or a solvate of said salt together with at least one pharmaceutically acceptable carrier or excipient.

6. A pharmaceutical composition for the treatment of a gastrointestinal disorder comprising an effective amount of the compound defined by claim 2 together with at least one pharmaceutically acceptable carrier or excipient.

7. A pharmaceutical composition for the treatment of a gastrointestinal disorder comprising an effective amount of the compound defined in claim 3 together with at least one pharmaceutically acceptable carrier or excipient.

8. A pharmaceutical composition for treating of a gastrointestinal disorder comprising an effective amount of the compound defined by claim 4 together with at least one pharmaceutically acceptable carrier or excipient.

* * * * *